United States Patent [19]

DelMar

[11] Patent Number: 4,465,879
[45] Date of Patent: Aug. 14, 1984

[54] PROCESS TO INSECTICIDE INTERMEDIATE

[75] Inventor: Eric G. DelMar, Hopewell, N.J.

[73] Assignee: FMC Corporation, Philadelphia, Pa.

[21] Appl. No.: 524,706

[22] Filed: Aug. 19, 1983

[51] Int. Cl.$^3$ ............................................. C07C 17/26
[52] U.S. Cl. .................................................... 570/190
[58] Field of Search ........................................ 570/190

[56] References Cited

U.S. PATENT DOCUMENTS 4,214,004  7/1980  Plummer .............................. 424/305
4,238,505  12/1980  Engel .................................. 424/305

OTHER PUBLICATIONS

M. Kumada, *Pure and Appl. Chem.*, 52, 669 (1980).
Mitchell et al., *Can. J. Chem.*, 58, 2584 (1980).
Sekiya et al., *J. Organometallic Chem.*, 118, 349 (1976).
*Tet. Lett.*, 21, 845 (1980).

*Primary Examiner*—Charles F. Warren
*Assistant Examiner*—Joseph A. Boska
*Attorney, Agent, or Firm*—R. L. Hansen; H. R. Ertelt

[57] ABSTRACT

A 3-halo-2-methylphenylmagnesium halide is cross-coupled with a halobenzene under heterogeneous conditions using palladium metal as catalyst, producing a 3-halo-2-methyl[1,1'-biphenyl].

7 Claims, No Drawings

PROCESS TO INSECTICIDE INTERMEDIATE

This invention is in the field of chemical processes; more specifically, cross-coupling an aryl Grignard reagent with a halobenzene in the presence of a heterogeneous palladium metal catalyst to produce a biphenyl compound.

Pyrethroid ester insecticides are of great commercial interest throughout the world. Both the carboxylic acid and alcohol moieties of these esters cover a wide range of structures. The alcohol, (2-methyl[1,1'-biphenyl]-3-yl)- methanol, affords a series of esters having especially attractive insecticidal efficacy when combined with appropriate carboxylic acids; for example, 3-(2,2-dihaloethenyl)-2,2-di- methylcyclopropanecarboxylic acids and 3-(2-chloro-3,3,3-trifluoro-1propenyl)-2,2-dimethylcyclopropanecarboxylic acid. Esters of these acids combined with (2-methyl[1,1'-biphenyl]-3-yl)-methanol are described in U.S. Pat. No. 4,214,004 and U.S. Pat. No. 4,238,505, respectively, the disclosures thereof being incorporated herein by reference.

Although pyrethroid esters of (2-methyl[1,1'-biphenyl]- 3-yl)-methanol have commercial potential, yields of the requisite (2-methyl[1,1'-biphenyl]-3-yl)-methanol from known preparative techniques have been too low to warrant commercialization. For example, U.S. Pat. No. 4,214,004 discloses an overall yield of about 15% beginning with 2-methyl-3-nitrobenzyl alcohol.

According to the multistep synthesis of which the present invention is the key step, the overall yield of (2-methyl[1,1'-biphenyl]-3-yl)-methanol is about 60 % utilizing a commercially available 2,6-dihalotoluene, i.e., 2,6-dichlorotoluene or 2-bromo-6-chlorotoluene, in the first step to produce a 3-halo-2-methylphenylmagnesium halide, i.e., 3-chloro-2-methyl- phenylmagnesium chloride or bromide, by conventional techniques. The 2,6-dihalotoluene preferably carries at least one chlorine atom in order to minimize self-coupling.

The key to success of the overall process lies in the next step in which the 3-halo-2-methylphenylmagnesium halide dissolved in an inert solvent is cross-coupled with a halobenzene under heterogeneous conditions employing palladium metal as a catalyst, producing a 3-halo-2-methyl-[1,1'-biphenyl], i.e., 3-chloro-2-methyl-[1,1'-biphenyl]. It is this step which is the process of this invention.

The 3-halo-2-methyl-[1,1'-biphenyl] can be converted to the desired (2-methyl[1,1'-biphenyl]-3-yl)-methanol by various methods. For example, the 3-halo-2-methyl-[1,1'-biphenyl] can be converted to a 2methyl([1,1'-biphenyl]-3-yl)-magnesium halide, which then yields the desired (2-methyl[1,1'-biphenyl]-3-yl)-methanol when treated with formaldehyde, processes which are well known in the art.

Although other techniques for preparing the Grignard reagent are known, the 3-halo-2-methylphenylmagnesium halide, preferably 3-chloro-2-methylphenylmagnesium chloride, is advantageously prepared in an inert solvent. Inert solvents suitable for use in the process include ethers, e.g., tetrahydrofuran and diethylether, as well as liquid tertiary amines, e.g., triethylamine. The so-prepared solution of the Grignard reagent is then preferably added slowly to a warm, stirred suspension of the palladium metal catalyst in the halobenzene.

Whereas the halobenzene may be bromobenzene or iodobenzene, bromobenzene is preferred. At least a 10 % molar excess of halobenzene should be used to maximize yield. The use of iodobenzene leads to more self-coupling to biphenyl, with a corresponding decrease in cross-coupling yield, than if bromobenzene is used.

Generally, a catalytic amount of palladium metal catalyst sufficient to contain about 0.01-1.0, preferably 0.02-0.5, mole percent palladium metal based on the Grignard reagent is sufficient, and larger amounts may actually lead to lower yields of the desired product. Although palladium metal, e.g., as commercially available palladium black, can be used, the small amounts required are difficult to weigh and handle, so it is usually desirable to employ palladium metal carried on a solid support such as carbon, alumina, silica, or clay. Palladium metal on either carbon or alumina as solid supports are available commercially and preferred for that reason. At the catalyst levels employed in this invention, catalyst recovery and recycling are not necessary.

The procedure for conducting the cross-coupling reaction of this invention is illustrated by the following Examples:

EXAMPLE 1

Palladium On Carbon As Catalyst

Bromobenzene (7.58 g, 48.3 millimoles) and 5% palladium on carbon (0.01 g, 4.83 micromole of palladium metal) was stirred under nitrogen at 100° C. To this was added dropwise during a 15 hour period 3-chloro-2-methylphenylmagnesium chloride (4.48 g, 24.2 millimoles) in dry tetrahydrofuran (15 ml), which has been prepared by the method of Mitchell and Yan, *Can. J. Chem.*, 58, 2584 (1980). The reaction mixture was stirred for two hours and then analyzed by vapor phase chromatography, which indicated 95.8 % of the Grignard reagent had reacted. Of the products which formed, 86.1% was 3-chloro-2-methyl[1,1' -biphenyl], a yield of 82.5% based on the Grignard reagent.

Other similar experiments utilizing palladium on carbon under conditions within the scope of this invention are summarized as follows:

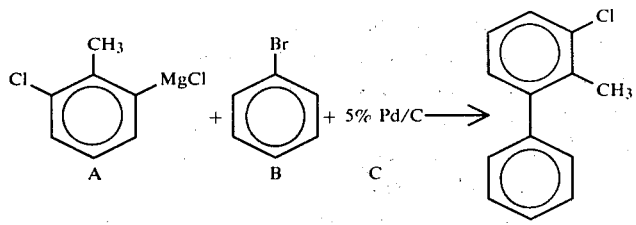

| | Reagents | | | Addition | Reaction[b] | | |
|---|---|---|---|---|---|---|---|
| Example | A (mmoles) | B (mmoles) | C[a] (mole %) | time (hr) | Time (hrs) | Temp (°C.) | Yield (%) |
| 2 | 24.2 | 120.8 | 0.5 | 1.5 | 4.0 | 80 | 73.7 |
| 3 | 24.2 | 60.4 | 0.1 | 20.0 | 20.0 | 80 | 77.6 |
| 4 | 24.2 | 48.3 | 0.1 | 2.5 | 2.5 | 100 | 81.3 |
| 5 | 24.2 | 48.3 | 0.01 | 5.5 | 5.5 | 120 | 54.6 |

[a]Mole % based on Grignard reagent.
[b]The reaction time is the total of the addition time, plus the time the reaction was stirred at the reaction temperature after complete addition.

EXAMPLE 6
Palladium On Alumina As Catalyst

Bromobenzene (18.9 g, 120.7 millimoles) and 5% palladium on alumina (0.25 g, 0.12 millimole of palladium metal) was stirred under nitrogen at 80° C. A solution of 3-chloro-2-methylphenyl- magnesium chloride (4.48 g, 24.2 millimoles) in dry tetrahydrofuran (15 ml) was added dropwise to the reaction mixture during a 1.25 hour period. After complete addition the mixture was analyzed by vapor phase chromatography. Analysis of the reaction mixture indicated 98% of the Grignard reagent had reacted. Of the products formed, 75.2% was 3-chloro-2- methyl[1,1'-biphenyl], a yield of 73.5% based on the Grignard reagent added.

What is claimed is:

1. A process for producing 3-chloro-2-methyl-[1,1'-biphenyl] which comprises cross-coupling a halobenzene with a solution of 3-halo-2-methylphenylmagnesium halide dissolved in an inert solvent in the presence of a catalytic amount of palladium metal under heterogeneous conditions.

2. The process of claim 1 wherein the palladium metal is carried on a solid support.

3. The process of claim 2 wherein said solid support is carbon.

4. The process of claim 2 wherein said solid support is alumina.

5. The process of claim 1 wherein said catalytic amount of palladium metal is 0.02–0.5 mole percent based on 3-halo-2-methylphenylmagnesium halide.

6. The process of claim 1 wherein the halobenzene is bromobenzene.

7. The process of claim 1 wherein the 3-halo-2-methylphenylmagnesium halide is 3-chloro-2methylphenylmagnesium chloride.

* * * * *